US00PP14928P2

(12) United States Plant Patent
Noodelijk

(10) Patent No.: US PP14,928 P2
(45) Date of Patent: Jun. 22, 2004

(54) CHRYSANTHEMUM PLANT NAMED 'CEARGOS'

(50) Latin Name: *Chrysanthemum morifolium*
Varietal Denomination: Ceargos

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 30 days.

(21) Appl. No.: 10/317,047

(22) Filed: Dec. 12, 2002

(51) Int. Cl.[7] ..... A01H 5/00
(52) U.S. Cl. ..... Plt./289

(58) Field of Search ..... Plt./289

(56) References Cited

PUBLICATIONS

UPOV–Rom hit on 'Argos', Plant Variety Database 2003/03.*

* cited by examiner

*Primary Examiner*—Anne Marie Grunberg
(74) *Attorney, Agent, or Firm*—Parkhurst & Wendel, L.L.P.

(57) ABSTRACT

A chrysanthemum plant named 'Ceargos' characterized by its medium sized blooms with yellow-orange ray florets and prolific branching; natural season flower date August 19–25; blooming for a period of 5 weeks.

3 Drawing Sheets

BACKGROUND OF THE INVENTION

'Ceargos' is a product of a breeding and selection program for outdoor pot mums (garden mums) that had the objective of creating new chrysanthemum cultivars with a decorative type flower, a natural season flower date around August 19–25, and blooming for a period of 5 weeks. The new plant of the present invention, a new and distinct cultivar of Chrysanthemum plant 'Ceargos', is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout, Holland in August 2000. The plant has been asexually reproduced by cuttings in greenhouses at Rijsenhout, Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
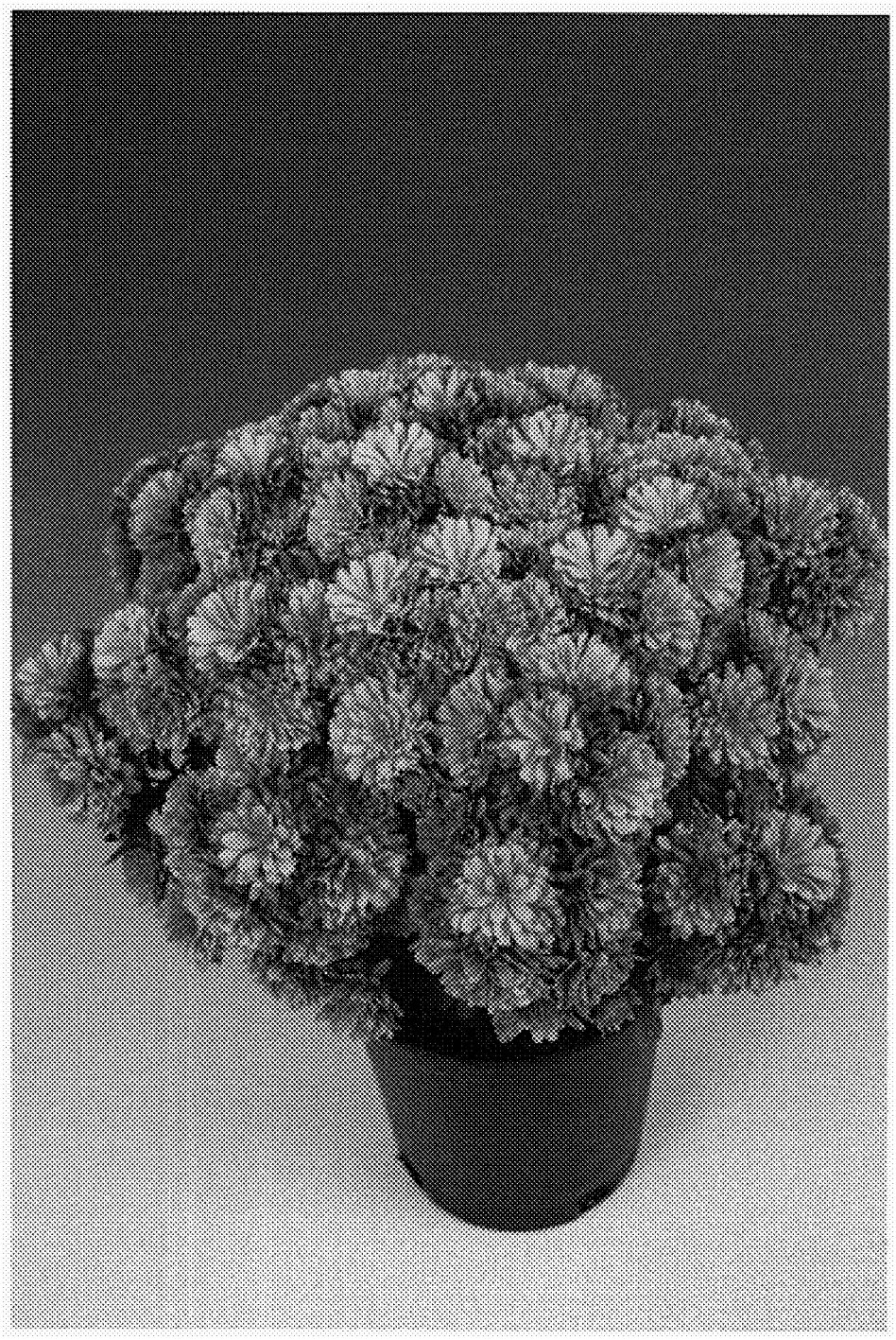
FIG. 1 shows a plant of the cultivar in full bloom.
Figure 2:
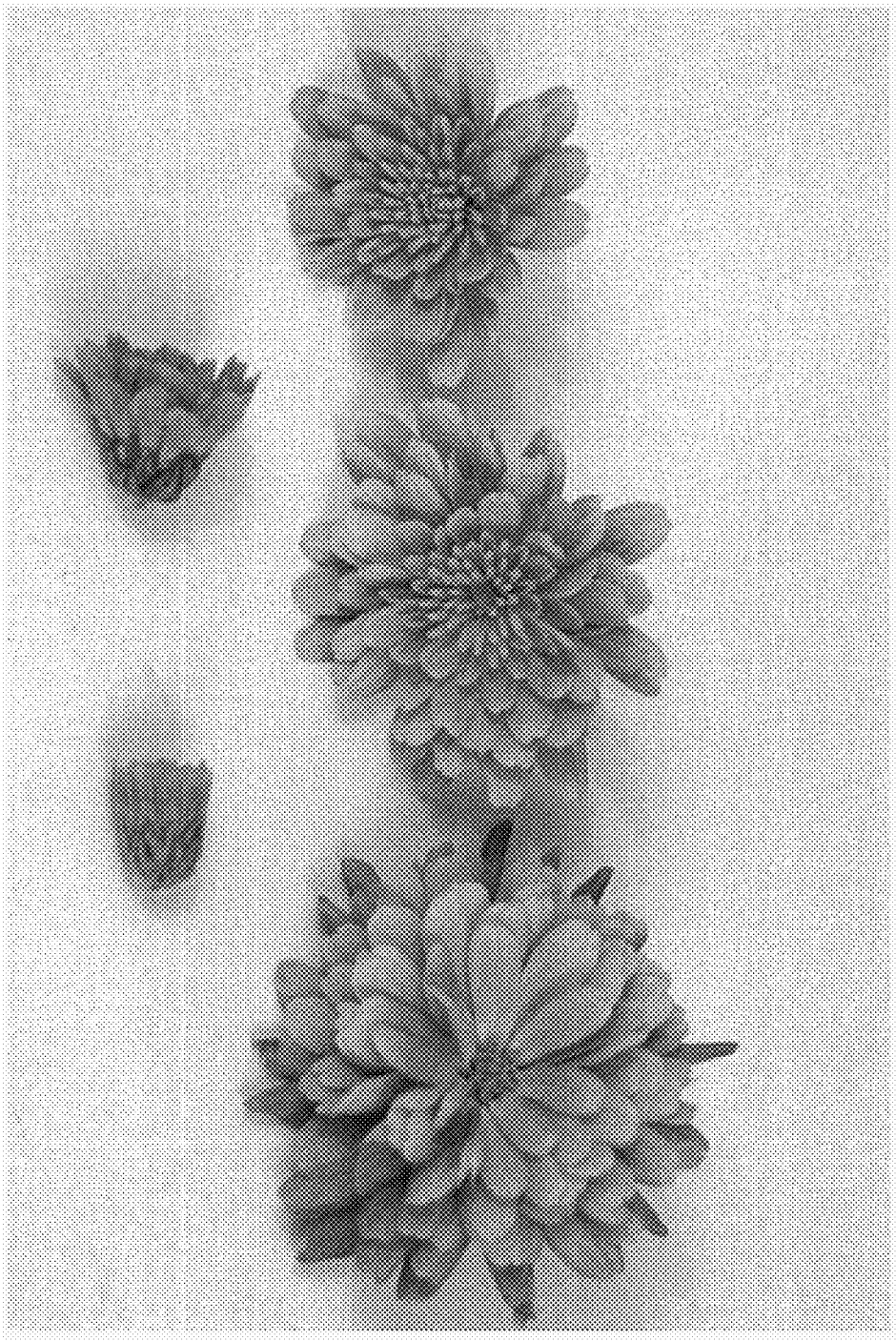
FIG. 2 shows the various stages of bloom of the new cultivar.
Figure 3:
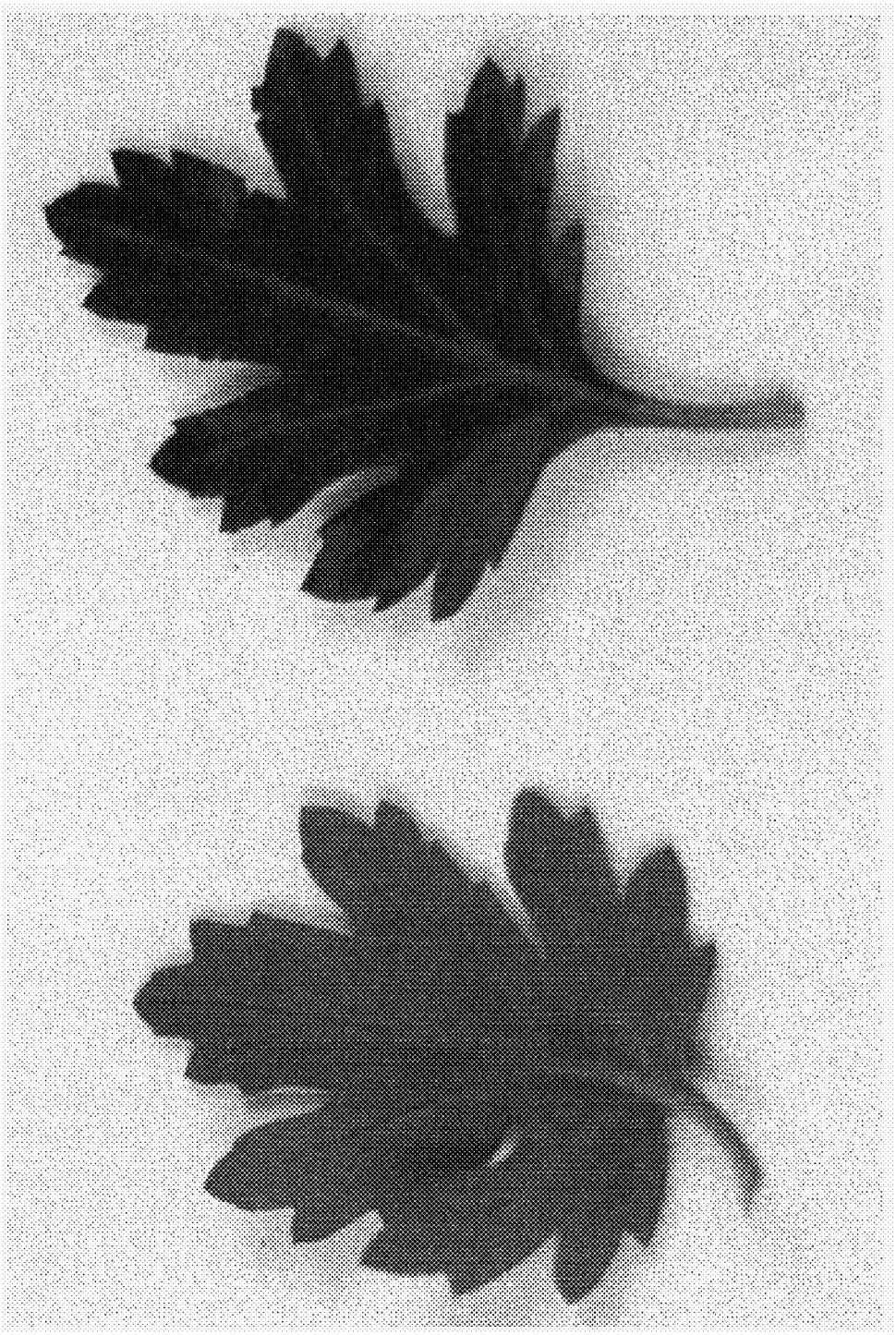
FIG. 3 shows the petiole and foliage of the new cultivar.

This new variety of chrysanthemum is of the botanical classification *Chrysanthemum morifolium.* The observations and measurements were gathered from plants grown out door in Rijsenhout, Holland under natural day length and temperature and planted week 22 in 2000 and 2001. The natural blooming date of this crop was August 19–25 (week 34). The average height of the plants was 26 cms. No growth retardants were used. No tests were done on disease or insect resistance or susceptibility. No tests were done on cold or drought tolerance. This new variety produces medium sized blooms with yellow-orange ray florets and a yellow center blooming for a period of 5 weeks.

From the cultivars known to inventor the most similar existing cultivar in comparison to 'Ceargos' is 'Taffy'. When 'Taffy' and 'Ceargos' are compared, the following differences are noticed: The differences of 'Taffy' and 'Ceargos' are (1) Natural blooming date. 'Ceargos' flowers earlier. (2) Bloom color. 'Ceargos' has a more even color.

The following is a description of the plant and characteristics that distinguish 'Ceargos' as a new and distinct variety. The color designations are taken from the plant itself. Accordingly, any discrepancies between the color designations and the colors depicted in the photographs are due to photographic tolerances. The color chart used in this description is: The Royal Horticultural Society Color Chart, 1995 edition.

Table 1. Botanical Description of cultivar 'Ceargos'

Bud:
- *Size.*—Medium; cross-section 1.4 cm, height 1.0 cm.
- *Outside color.*—Yellow-orange 22 A.
- *Involucral bracts.*—2 rows, length 13–15 cm, width 3 mm.
- *Involucral bracts among disc-florets.*—Not present.
- *Involucral bracts color.*—Yellow-green 148 C.

Bloom:
- *Type.*—Decorative.
- *Height.*—Medium, 1.5 cm.
- *Size.*—Medium.
- *Fully expanded.*—3.5–4.0 cm.
- *Number of blooms per branch.*—Approx. 6 blooms per branch.
- *Performance on the plant.*—5 weeks.
- *Seeds (if crossed).*—Produced in small quantities, ovate grey-brown 199A, 1½ mm in length.
- *Fragrance.*—Typical chrysanthemum, slight.

Color:

*Center of the flower* (*disc-florets*).—Immature yellow-orange 16 A. Mature yellow-orange 14 A.

*Color of upper surface of the ray-florets.*—Yellow orange 17 A.

*Color of the lower surface of the ray-florets.*—Yellow-orange 22 A.

*Tonality from distance.*—A garden mum with yellow-orange flowers and a yellow disc.

*Color of the upper surface of the flowers after aging of the plant.*—Yellow-orange 22 B.

Ray florets:

*Texture.*—Upper and under side smooth.

*Number.*—100–110.

*Cross-section.*—Flat.

*Longitudinal axis of majority.*—Straight.

*Length of corolla tube.*—Short, 0.3 cm.

*Ray-floret margin.*—Entire.

*Ray-floret length.*—1.6–1.8 cm.

*Ray-floret width.*—0.4 cm.

*Ratio length/width.*—High.

*Shape of tip.*—Rounded.

Disc florets:

*Disc diameter.*—0.3 cm.

*Distribution of disc florets.*—Present in small amounts.

*Shape.*—Tubular.

*Color.*—Yellow-orange 24A.

*Receptacle shape.*—Domed raised.

Reproductive organs:

*Stamen* (*present in disc florets only*).—Thin, 3 mm in lenght.

*Stamen color.*—Yellow-green 144 A.

*Pollen.*—Sometimes present.

*Pollen color.*—Yellow 7 A.

*Styles.*—Thin.

*Style color.*—Yellow-green 144 A.

*Style length.*—4 mm.

*Stigma color.*—Yellow-green 144 A.

*Stigma width.*—1 mm.

*Ovaries.*—Enclosed in calyx.

Plant:

*Shape.*—Grown as a spray-type pot-mum, outdoor mounded and round.

*Growth habit.*—Spreading.

*Growth rate.*—Moderate.

*Height.*—26 cm.

*Width.*—30–32 cm.

*Stem color.*—Yellow-green 147A.

*Stem strength.*—Strong.

*Stem brittleness.*—Present.

*Stem anthocyanin coloration.*—Absent.

*Length of lateral branch.*—From top to bottom 11–12 cm.

*Lateral branch color.*—Yellow-green 147 A.

*Lateral branch, attachment.*—Brittle.

*Branching* (*average number of lateral branches*).—Prolific with 8–9 breaks after pinching.

*Peduncle length.*—5 cm.

*Peduncle color.*—Yellow-green 147A.

*Natural season blooming date.*—August 19–25.

Foliage:

*Color.*—Upper side yellow-green 147A. Under side yellow-green 147C.

*Size.*—Medium.; length 4.0 cm, width 5.0 cm.

*Quantity* (*number per lateral branch*).—12–14.

*Shape.*—Ovate.

*Texture upper side.*—Glabrous.

*Texture under side.*—Pubescent.

*Venation arrangement.*—Palmate.

*Shape of the margin.*—Serrated.

*Shape of base of sinus between lateral lobes.*—Acute.

*Margin of sinus between lateral lobes.*—Diverging.

*Shape of base.*—Truncate.

*Apex.*—Mucronate.

TABLE 2

Differences with the comparison varieties

| | 'CEARGOS' | 'TAFFY' |
|---|---|---|
| Color of the upper surface of the ray-florets | Yellow-orange 17A | Center orange 26A<br>Outer florets yellow orange 17A |
| Natural blooming date | August 19–25 | October 3–10 |

I claim:

1. A new and distinct variety of chrysanthemum plant as described and illustrated.

* * * * *